United States Patent [19]
Singer et al.

[11] Patent Number: 5,866,331
[45] Date of Patent: Feb. 2, 1999

[54] SINGLE MOLECULE DETECTION BY IN SITU HYBRIDIZATION

[75] Inventors: Robert H. Singer, Shrewsbury; Andrea M. Femino, South Barre, both of Mass.

[73] Assignee: University of Massachusetts, Boston, Mass.

[21] Appl. No.: 546,072

[22] Filed: Oct. 20, 1995

[51] Int. Cl.$^6$ .............................. C12Q 1/68; G02B 21/34; G01J 1/58
[52] U.S. Cl. ............................ 435/6; 250/459.1; 359/396
[58] Field of Search .................................. 435/6; 359/396; 422/82.08; 250/459.1

[56] References Cited

U.S. PATENT DOCUMENTS 5,047,968  9/1991  Carrington et al. ..................... 364/574

OTHER PUBLICATIONS

Viegas–Pequignot et al., "Mapping of single–copy DNA sequences on human chromosomes by in situ hybridization with biotinylated probes: Enhancement of detection sensitivity by intensified–fluorescence digital–imaging microscopy," *Proc. Natl. Acad. Sci. USA*. 96:582–586 (1989).

Taneja et al., "Poly(A) RNA codistribution with microfilaments: Evaluation by in situ hybridization and quantitative digital imaging microcopy", *J. Cell Biol.* 119:1245–1260, Dec. 1992.

Carrington et al., "Superresolution three–dimensional images of fluorescence in cells with minimal light exposure", *Science* 268: 1483–1487, Jun. 1995.

Shotton, D.M., "Electronic light microscopy: present capabilities and future prospects", *Histochem. Cell. Biol.* 104: 97–137, Sep. 1995.

Femino et al., "Detection of single actin messenger RNAs in situ using high resolution digital imaging microscopy", *Molec. Biol. Cell* 6 (suppl. S): 1796, Nov. 1995.

Betzig et al., "Single Molecules Observed by Near–Field Scanning Optical Microscopy," *Science* 262:1422–1425 (1993).

Clementi et al., "Quantitative molecular methods in virology," *Arch. Virol.* 140:1523–1539 (1995).

Funatsu et al., "Imaging of single flourescent molecules and individual ATP turnovers by single myosin molecules in aqueous solution," *Nature* 374:555–559 (1995).

Nie et al., "Probing Individual Molecules with Confocal Fluorescence Microscopy," *Science* 266:1018–1021 (1994).

Peck et al., "Single–molecule fluorescence detection: Autocorrelation criterion and experimental realization with phycoerythrin," *Proc. Natl. Acad. Sci. USA* 86:4087–4091 (1989).

Taneja et al., "Foci of Trinucleotide Repeat Transcripts in Nuclei of Myotonic Dystrophy Cells and Tissues," *J. Cell Biology* 128:995–1002 (1995).

Trautman et al., "Near–field spectroscopy of single molecules at room temperature," *Nature* 369:40–42 (1994).

*Primary Examiner*—Jasemine C. Chambers
*Assistant Examiner*—Scott D. Priebe
*Attorney, Agent, or Firm*—Fish & Richardson P.C.

[57] ABSTRACT

Disclosed are methods for accurately determining the total emission intensity of a single fluorochrome, under imaging conditions, using a digital imaging fluorescence microscopy system. Also disclosed are methods for detecting and localizing probe-target molecule binding. The detection method has sufficient resolution and sensitivity to locate and detect a single target-bound probe.

27 Claims, 3 Drawing Sheets

SINGLE MOLECULE DETECTION BY IN SITU HYBRIDIZATION

STATEMENT AS TO FEDERALLY SPONSORED RESEARCH

Work on this invention was supported, in part, with funds from the United States Government (NIH grant HD18066). The government therefore has certain rights in the invention.

FIELD OF THE INVENTION

This invention relates to cell biology, microscopy, and digital imaging.

BACKGROUND OF THE INVENTION

High resolution localization of single-copy nucleic acid sequences by fluorescence in situ hybridization has been described. See, e.g., Lawrence et al., *Cell*, 52: 51–61 (1988). Such methodology, however, is based on the use of a heterogenous population of relatively large probes, i.e., typically up to about 1,000 nucleotides. The probes, typically labeled by nick translation, carry undefined numbers of fluorochromes. The probes typically are designed to hybridize end-to-end, along a sequence of several thousand nucleotides within or near the target gene. In addition, such probes can hybridize to one another, forming large random aggregations due to "networking" at the target gene.

Although such methodology can detect the presence of a single copy of a nucleotide target sequence, the target sequence must be several thousand nucleotides long. Moreover, there is no stoichiometric relationship between the target sequence and fluorescence intensity.

SUMMARY OF THE INVENTION

We have discovered a method for determining the total fluorescence intensity ("TFI") of a single fluorochrome, under imaging conditions, in a digital imaging microscopy system. Based on our discovery of a method for accurately determining the total fluorescence intensity of a single fluorochrome under imaging conditions, the invention features a digital imaging fluorescence microscopy detection method for detecting probe-target molecule binding. The detection method is sufficiently sensitive to detect a single bound probe molecule.

In general, the invention features a method for digital imaging fluorescence microscopy detection of an individual probe bound to a target molecule in a sample. The method includes the steps of (a) obtaining a fluorochrome-labeled probe wherein the number of fluorochromes per probe is predetermined; (b) contacting the labeled probe with a target molecule under conditions allowing the labeled probe to bind to the target molecule; (c) removing unbound labeled probes from labeled probes bound to target molecules; (d) detecting, by digital imaging fluorescence microscopy, the labeled probe bound to the target molecule, wherein the digital imaging fluorescence microscopy includes digitally recording a series of optical sections; (e) determining the total fluorescence intensity per fluorochrome under imaging conditions; (f) determining the total fluorescence intensity per probe from the total fluorescence intensity per fluorochrome; (g) producing a prepared image from the series of optical sections; (h) producing a restored image; (i) identifying discrete objects in the restored image, the objects corresponding to target molecules; (j) determining the presence of one or more probes in an object, thereby detecting an individual probe bound to a target molecule in a sample.

The restored image can be produced by subjecting a prepared image to exhaustive photon reassignment. Further, a threshold can be applied to the restored image. In this method, the probe can be an oligonucleotide, e.g., from 20 to 200, and preferably from 40 to 100 nucleotides, linked to a fluorochrome label, the target molecule can be a nucleic acid, e.g., a DNA or RNA molecule, and the binding can be in situ nucleic acid hybridization. The fluorochrome label is preferably covalently attached to a functional group, e.g., a primary amino group, on a modified base incorporated into the oligonucleotide. The oligonucleotide can include a multiplicity of modified bases with attached fluorochromes, e.g., incorporated at intervals of seven to thirteen base positions in the nucleotide sequence of the oligonucleotide.

In this method, the presence of one or more probes in an object is determined based on the total fluorescence intensity of the object and the total fluorescence intensity per probe.

The total fluorescence intensity per fluorochrome under imaging conditions can be determined by a method including the steps of (a) providing a microscope slide and coverslip; (b) providing on the surface of the microscope slide a first fluorescence point source; (c) providing on the surface of the coverslip a second fluorescence point source; (d) preparing a standard solution containing a known concentration of fluorochrome-labeled probes; (e) placing a suitable volume of the standard solution between and in contact with the microscope slide and the coverslip, the first fluorescence point source and the second fluorescence point source being within the field of view of the digital imaging microscopy system; (f) determining a distance between the first and second fluorescence point sources, thereby obtaining a z axis distance between the microscope slide and the coverslip; (g) determining an imaged volume by determining the product of an x axis distance, a y axis distance, and the z axis distance; (h) determining the total amount of probe fluorescence from the imaged volume; (i) calculating the total number of probes in the imaged volume using (1) the known concentration of probes in the standard solution, and (2) the imaged volume; and (j) dividing the total amount of probe fluorescence from the imaged volume by the number of fluorochromes in the imaged volume to determine the total fluorescence intensity of a single fluorochrome under imaging conditions.

The threshold can be determined and applied by (a) preparing a restored image of a negative control cell subjected to a mock in situ hybridization protocol wherein no probe is present; (b) obtaining a frequency distribution of light in the negative control cell and calculating the mean and standard deviation of the frequency distribution; (c) selecting a total fluorescence intensity threshold value based on the mean and standard deviation; (d) excluding all optical data other than that originating from within the sample cell, thereby producing a masked image; and (e) setting to a value of zero all pixels whose total fluorescence intensity value is below the total fluorescence intensity threshold value in the masked image.

The invention further features a method for determining the total fluorescence intensity of a single fluorochrome in a digital imaging microscopy system, under imaging conditions. This method includes the steps of (a) providing a microscope slide and coverslip; (b) providing on the surface of the microscope slide a first fluorescence point source; (c) providing on the surface of the coverslip a second fluorescence point source; (d) preparing a standard solution containing a known concentration of fluorochrome-labeled probes; (e) placing a suitable volume of the standard solution between and in contact with the microscope slide and the coverslip, the first fluorescence point source and the second fluorescence point source being within the field of view of the digital imaging microscopy system; (f) determining a distance between the first and second fluorescence point sources, thereby obtaining a z axis distance between the microscope slide and the coverslip; (g) determining an imaged volume by determining the product of an x axis distance, a y axis distance, and the z axis distance; (h) determining the total amount of probe fluorescence from the imaged volume; (i) calculating the total number of probes in the imaged volume using (1) the known concentration of probes in the standard solution, and (2) the imaged volume; and (j) dividing the total amount of probe fluorescence from the imaged volume by the number of fluorochromes in the imaged volume to determine the total fluorescence intensity of a single fluorochrome under imaging conditions.

The method of the invention can be used to diagnose a viral infection, when the target nucleic acid is a viral nucleic acid, e.g., from HIV. The method can also be used to diagnose a genetic defect, e.g., a trinucleotide repeat expansion, when the target nucleic acid is a chromosome.

In another embodiment, the invention features, a microscope slide or coverslip including fluorescent material on at least one surface, the material being deposited on the surface as a discrete spot, the spot having a diameter and a thickness between 1 and 400 nanometers.

As used herein, "background subtraction" means removal of light-dependent noise after dark current subtraction.

As used herein, "dark current subtraction" means the removal of artifacts caused by electrical current in a CCD in the absence of light.

As used herein, "first optical section" means the earliest recorded optical section in a given series of optical sections.

As used herein, "fluorochrome" means a molecule or moiety that emits light of a second predetermined wavelength upon absorption of light of a first predetermined wavelength.

As used herein, "imaged volume" means the sample volume from which fluorescent light is collected in a digital imaging microscopy system.

As used herein, "mounting medium" means the solution in which a fluorescently-labeled probe exists during sample imaging.

As used herein, "object" means a contiguous collection of non-zero voxels in a restored image after an appropriate threshold has been determined and applied.

As used herein, "point spread function" (or "PSF") means a mathematical description of the blurring function of a microscope. The point spread function is sometimes called the "optical impulse response."

As used herein, "prepared image" means an image subjected sequentially to: (1) dark current subtraction, (2) background subtraction, and (3) normalization to the first optical section.

As used herein, "restored image" means a prepared image whose out-of-focus light has been reassigned to its point source.

As used herein, "voxel" means the fundamental unit of a three-dimensional digital image.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

The present invention provides a method for accurate quantitation of the TFI of a single fluorochrome when the fluorochrome is attached to a probe and observed by digital imaging fluorescence microscopy, under imaging conditions. That accurate quantitation allows digital imaging fluorescence microscopy and exhaustive photon reassignment to be used for the detection of a single fluorochrome-labeled probe bound to a target molecule. As few as five fluorochromes on a single probe provide a sufficiently strong signal for detection of that single probe.

The target molecule is preferably a nucleic acid molecule comprising a sequence of interest. The sequence of interest can be as short as about 20 nucleotides. The fluorochrome-labeled probe is preferably a synthetic oligonucleotide complementary to the sequence of interest in a target molecule. Preferably, the labeled oligonucleotide probe binds to the target molecule in a conventional in situ hybridization protocol. If needed for added signal intensity, a non-hybridizing "tail" containing fluorochromes can be added to the hybridizing portion of an oligonucleotide probe.

The present invention can be used to localize and detect quantitatively the presence of one or more target molecules, when the target-probe binding stoichiometry is already known, e.g., to determine by in situ hybridization whether a diploid cell contains none, one or two copies of a particular allele. In such an embodiment of the invention, in situ hybridization can be used to interrogate a cell for the presence of a single copy of a specific nucleotide sequence as short as about 20 nucleotides.

Alternatively, this invention can be used to determine the target-probe binding stoichiometry, where the stoichiometry is not already known. For example, a trinucleotide repeat $(CTG)_n$ in the 3' untranslated region of the human Mt-PK gene is expanded in persons with myotonic dystrophy. The normal number of repeats, i.e., about 5–27, expands to 50–2,000 in the disease state. The size of the expansion correlates with the severity of the disease symptoms. The number of fluorescently-labeled trinucleotide repeat probes binding to an Mt-PK gene in a sample cell, i.e., the target-probe binding stoichiometry, can be determined using the present invention. The binding stoichiometry provides a direct indication of the size of a trinucleotide repeat expansion.

Although preferred embodiments of the invention involve in situ hybridization of a fluorescently-labeled oligonucleotide probe and a target nucleic acid molecule, the scope of the invention is not limited to in situ hybridization. The invention can be practiced using specific binding interactions other than nucleic acid hybridization, as long as one of the binding partners is a fluorochrome or is conjugated to a fluorochrome label. For convenience and clarity, however, the following discussion is presented primarily in terms of nucleic acids and in situ hybridization.

The invention uses a highly sensitive charge-coupled device (CCD) camera to collect light from a fluorescence microscope. The collected light is recorded as a series of optical sections from a sample. Much of the light in any given optical section is out-of-focus light that has spread from numerous individual point sources. Therefore, an unprocessed optical section is inevitably convoluted, and image resolution is diminished accordingly. Using a standard 3D image restoration algorithm known as exhaustive photon reassignment ("EPR"), a restored (i.e., deconvoluted) image is generated from a series of optical sections. EPR reassigns all of the collected light in a series of optical sections to the original point sources of the light. Fluorescent beads placed in the imaged sample are used to obtain a "point spread function," which is used in the EPR algorithm.

In addition to enhancing resolution, EPR enhances the sensitivity of detection, because it utilizes all of the light collected. This is in contrast to confocal methods, where a significant fraction of the light signal is never received by the detector.

Despite the enhanced contrast and resolution of a restored image, there is no way to determine the number of probes responsible for a particular point of fluorescence, unless the TFI of a single probe—in the imaging environment—is known. The present invention provides a method of determining the TFI per fluorochrome (or per probe bearing a known number of fluorochromes) in an imaging environment.

Once the TFI per fluorochrome is known, quantitating the intensity of a fluorescence point source allows the number of fluorochromes (and therefore the number of probes) bound at that point source to be determined.

An analysis of the points of fluorescence in a restored image can be presented in the form of a "heat map." In a heat map, points with a fluorescence intensity corresponding to one probe are displayed in the coolest hue. Points with fluorescence intensities corresponding to two probes, three probes, etc., are displayed in successively warmer hues.

The ability to detect single copies of nucleotide sequences of interest with single oligonucleotide probes conjugated to fluorochromes means that probes labeled with fluorochromes of different colors can be used to detect different sequences of interest simultaneously. For example, differing sequences located near opposite ends of a single mRNA molecule can be simultaneously detected in different colors.

By virtue of its ability to detect a single labeled oligonucleotide probe, the present invention is useful as a tool in biological research. For example, this invention enables rapid and specific detection of a single specific mRNA splice junction by means of an oligonucleotide that spans the junction. Detection of a specific mRNA splice junction demonstrates that a specific mRNA processing event has occurred.

The present invention can also be used as a rapid and powerful clinical diagnostic tool. For example, this invention can be used to diagnose infection with a virus, e.g., HIV. When used to diagnose viral infection, the present invention is more sensitive than conventional in situ hybridization methods. Moreover, by its ability to detect a single copy of a specific nucleotide sequence as short as about 50 nucleotides, the present invention enables diagnosis not only as to infection with a particular type of virus, but also as to infection with a particular strain of virus.

Digital Imaging Fluorescence Microscopy and Data Analysis

Digital imaging fluorescence microscopy is known in the art. Complete digital imaging fluorescence microscopy systems, or components for assembly of a complete system, are commercially available. A basic digital imaging fluorescence microscopy system includes the following operationally linked components: (1) a conventional fluorescence microscope, (2) a means for optical sectioning, e.g., a micrometer, (3) an optical detector, e.g., a CCD camera, and (4) a digital computer to store optical data. The foregoing basic components are commercially available. The operational linkage of the basic components is within ordinary skill in the art. Moreover, complete digital imaging fluorescence microscopy systems are commercially available (Scanalytics, Billerica, Mass.).

Methods and published software for data analyses carried out in the practice of the present invention are known in the art. A preferred software package is known as Data Analysis and Visualization Environment ("DAVE") Release 0.7 (May 18, 1994). DAVE was written by Jeff Collins nd Lawrence M. Lifshitz and has been published by the University of Massachusetts Medical School.

Basic references on digital image processing include the following: John C. Russ, *The Image Processing Handbook*, 2d ed., CRC Press, Boca Raton, Fla., (1995); and Kenneth R. Castleman, *Digital Image Processing,* Prentice-Hall, Inc., Englewood Cliffs, N.J., (1979).

Determination of Total Fluorescence Intensity (TFI) of Single Fluorochrome Under Imaging Conditions The TFI of a single fluorochrome under imaging conditions can be determined by at least three different methods.

The first method is based on accurately determining the imaged volume (described below), and measuring the sum TFI of all the fluorochromes in the imaged volume. The sum TFI is based on a representative optical section of a probe standard solution.

The following is a preferred procedure for determining the sum TFI from a representative optical section of a probe standard solution. The objective is set at the z axis midpoint, using the micrometer. Preferably, light is excluded during this step. The appropriate optical filter set is selected. A single optical section of the probe solution is acquired by exposing the probe solution to excitation for a time t, which is equal to the exposure time for each section in the series of optical sections of the imaged samples. This single optical section is subjected to dark current subtraction only. All pixels in the optical section are summed, e.g., with a standard "region of interest" algorithm. The total number of probe molecules in the imaged volume and the total number of fluorochromes in the imaged volume is calculated (number of fluorochromes per probe molecule multiplied by number of probe molecules). The sum TFI of the representative optical section is divided by the total number of fluorochrome molecules in the imaged volume.

The resulting value is defined as the TFI of a single fluorochrome under a given set of imaging conditions. "Imaging conditions" refers to the optical characteristics of the particular microscope used, exposure time (t), cover slip, microscope slide, mounting medium, and the intramolecular environment of the fluorochrome-probe conjugate.

The TFI obtained by the foregoing procedure is normalized to a value for a single conjugated fluorochrome whose image is acquired through a series of optical sections and restored using EPR. To accomplish this, the TFI is multiplied by the number of optical sections of the PSF used to restore a series of optical sections from the same imaging session. The result is a corrected TFI value which is used to determine the number of probe molecules binding to a target molecule in a restored image.

A second method for determining the TFI of a single fluorochrome under imaging conditions is based on a bona fide single copy genetic locus in a sample cell, e.g., the rat beta-actin gene. Several oligonucleotide probes (total number=n) capable of hybridizing to non-overlapping, non-transcribing regions of the selected single copy genetic locus are synthesized. A preferred probe length is about 40–80 nucleotides. The preferred number of non-overlapping probes (n) is about 5–10. The probes are equivalently labeled with a predetermined number of fluorochromes (m). Preferably the fluorochrome label used is CY3. A sample cell containing the selected single copy locus is subjected to in situ hybridization using a mixture containing equimolar amounts of all the probes. A restored image is produced and the TFI of each discrete object in the restored image is determined. A continuous TFI range representing from 1 to n probes hybridized at the selected gene is thereby obtained in the restored image. It is assumed that the uppermost TFI value in the continuous TFI range represents the selected gene with n probes hybridized. That TFI value is divided by the maximum total number of fluorochromes that can be bound to the selected gene (i.e., n×m), to obtain the TFI per fluorochrome.

In a third method for determining the TFI per fluorochrome under imaging conditions, fluorochrome-labeled probe molecules are allowed to adhere to the surface of a microscope slide or coverslip. In this method, a dilute solution of a fluorochrome-labeled probe is prepared.

When the fluorochrome-labeled probe is an oligonucleotide, the preferred dilute solution is mounting medium containing the oligonucleotide at a final concentration in the range of 3.0 to 20 picograms per microliter. This concentration range provides approximately 25 pixels per probe molecule, assuming: (1) all of the probe molecules in a 5 microliter volume of the solution adsorb onto the surface of a 22×22 mm glass coverslip, and (2) the probe length is approximately 60 nucleotides. If the probe molecule's mass differs substantially from the mass of a 60-nucleotide probe, the above concentration range is adjusted accordingly. Such adjustment is within ordinary skill in the art.

It has been empirically observed that the probe molecules adsorb preferentially to the coverslip instead of the microscope slide. If the probe molecules were to show equal preference for each of the two surfaces, there would be, on the average, 50 pixels per probe molecule.

Time is allowed for essentially complete adsorption of probe molecules onto the glass surface. A preferred time allowed for this adsorption is at least overnight. Preferably, during this adsorption time period, the slide is kept in darkness. More preferably, the slide is also kept a temperature below room temperature but above the freezing point of the probe-containing solution between the slide and coverslip.

Determination of Imaged Volume

Figure 1:
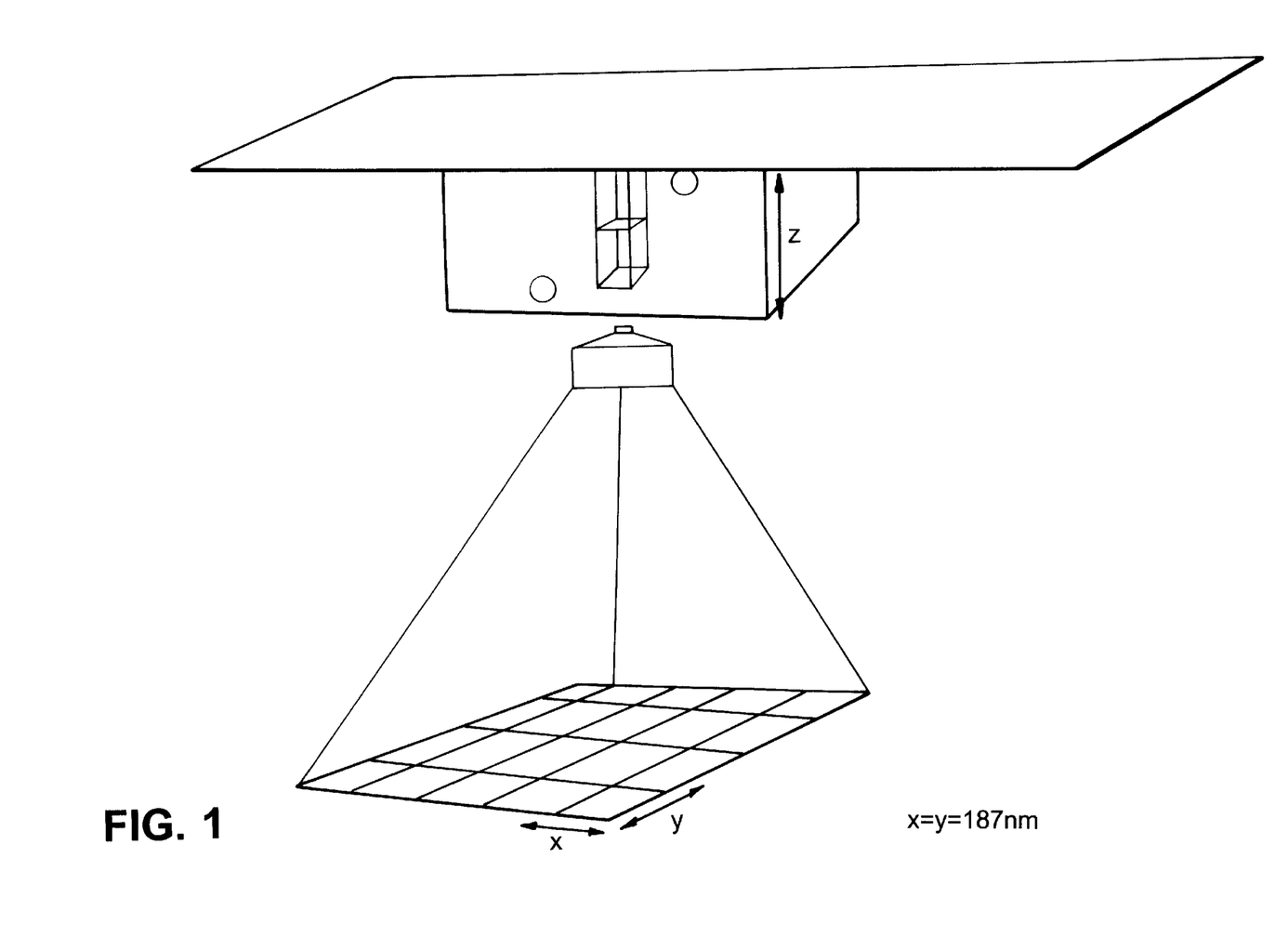
FIG. 1 is a schematic diagram of a portion of a digital imaging microscopy system. Depicted (top to bottom) are: the microscope slide, fluorescent bead on surface of microscope slide, sample solution (stippled area), imaged volume (outlined in white), a single optical section within the imaged volume (outlined in black), coverslip (at bottom edge of stippling), microscope objective, and CCD.

As shown in FIG. 1, the imaged volume 10 is the three-dimensional portion of the sample 12 from which fluorescent light is collected in a digital imaging fluorescence microscopy system. The x axis and the y axis of the imaged volume are parallel to the flat surfaces of the microscope slide 14 and the coverslip 16. The z axis is perpendicular to the microscope slide and the coverslip.

The lengths of the x and y axes (i.e., "the x axis distance" and "the y axis distance") are determined by the pixel size and number. Accordingly, x axis distance and the y axis distance (typically equal) are known, for any particular digital imaging microscopy system. In contrast, the z axis distance must be determined empirically. The present invention provides a method for accurate determination of the z axis distance.

Preferably, the z axis distance is measured immediately before the acquisition of a single optical section of a probe solution (of known concentration) in the imaged volume. The z axis distance is preferably measured in a method comprising the steps of:

(a) providing a microscope slide and coverslip;

(b) providing on the surface of said microscope slide a first fluorescence point source;

(c) providing on the surface of said coverslip a second fluorescence point source;

(d) preparing a standard solution containing a known concentration of fluorochromes;

(e) placing a suitable volume of said standard solution between and in contact with said microscope slide and said coverslip, said first fluorescence point source and said second fluorescence point source being within the field of view of said digital imaging microscopy system;

(f) focusing on said first fluorescence point source and recording a first micrometer value;

(g) focusing on said second fluorescence point source and recording a second micrometer value (h) subtracting one micrometer value from the other micrometer value, thereby obtaining a z axis distance between said microscope slide and said coverslip.

Preferably, the first and second fluorescence point sources are fluorescently labeled beads (18 and 20 in FIG. 1) resting on the surfaces of the microscope slide 14 and coverslip 16. Preferably, the beads are essentially spherical, with a diameter of 50 to 800 nanometers. More preferably, the diameter is from 100 to 400 nanometers. Most preferably, the diameter is approximately 200 nanometers. When suspended in an aqueous solution, such beads randomly settle onto glass surfaces. A field is selected which has at least one bead on each of the two parallel surfaces, i.e., the microscope slide and the coverslip.

Suitable beads are commercially available with various fluorochrome labels (Molecular Probes, Inc., Eugene, Oreg.). Preferably, the beads are selected to have fluorescence excitation and emission wavelengths distinct from those of the fluorochrome labeled probe molecules in the sample to be imaged. This avoids photobleaching of the probe molecules during the z distance measurement.

With a typical fluorescence microscope equipped for optical sectioning, the following procedure is preferred. A bead on the coverslip surface, i.e., the surface closest to the objective of an inverted microscope, is brought into focus. The micrometer reading is adjusted to a value close to 0.00. This sets the eddy current sensor in the center of its detection range, which typically extends from −25.00 to +25.00 micrometers. The exact reading is recorded when the bead is determined to be in focus, i.e., it has a maximum TFI at a single pixel when an image is acquired. The bead on the far surface is then brought into focus, and a second micrometer reading is recorded. The mean z distance is calculated immediately. To calculate the exact z distance, a correction of 0.20 micrometers is added to the calculated z distance to account for the diameter of the bead.

The z distance can be measured by means other than beads. For example, microscope slides and coverslips can be produced with fluorescent spots of fluorescent material of a suitable diameter and thickness deposited directly on their surfaces. Preferably, the spots have a diameter and thickness between one and 400 nanometers. Deposition of suitable fluorescent spots on slides and coverslips is within ordinary skill in the art. See, e.g., Pearson et al., Science 270: 68–69 (1995).

Determination of Point Spread Function

The optical parameters for a microscope can be described in terms of the direct-space point spread function ("PSF"). Principles and procedures relating to PSF are within ordinary skill in the art.

One approach to determining the PSF of a microscope is to directly image single fluorescent beads with a diameter of 0.1 micrometer. Since this diameter is smaller than the resolution limit, the beads effectively behave as point objects. For a discussion of PSF in digital imaging fluorescence microscopy, see, e.g., Hiraoka et al., *Science* 238: 36–41 (1987).

Exhaustive Photon Reassignment (EPR)

EPR is a standard mathematical technique used to generate a restored image from a series of optical sections. EPR is described by Carrington et al. in U.S. Pat. No. 5,047,968. EPR can be carried out on a conventional computer system, using commercially available software (Scanalytics, Billerica, Mass.).

Establishment of Threshold

A TFI threshold is established by setting to zero all pixels with values less than a minimum TFI. The appropriate threshold level is determined by analyzing the TFI frequency distribution of non-zero pixels in a negative control cell which has been subjected to a mock hybridization and restored with a scaling of 1.0.

Nuclei have the most consistent diffuse background free of sporadic intense granular or vesicular autofluorescence which is frequently found in the cytoplasmic regions of the cell. Therefore, nuclei provide a representative background level to establish a threshold. The TFI values in the imaged control nuclei or cytoplasm represent various background sources of illumination such as scattered light and low levels of cellular autofluorescence. This low level background produces a very nearly contiguous signal throughout the restored image. The background noise must be eliminated by a threshold to accomplish the analysis of discrete point sources of light.

When using CY3 as the fluorochrome label, a TFI value 3 standard deviations above the mean TFI per pixel in images from a negative control cell is the preferred threshold. This threshold eliminates greater than 95% of the low level background pixels, but does not approach the intensity value of a bona fide signal. The threshold value is adjusted by the appropriate scaling factor for images which have been restored with the autoscaling option. This conservative thresholding does not completely eliminate background signal.

Oligonucleotide Probe Design, Synthesis, and Labeling

The basic principles of oligonucleotide probe design and synthesis are well known. Those basic principles apply generally to the design and synthesis of oligonucleotide probes used in this invention.

This invention includes an essentially unlimited number of different oligonucleotide probes. For example, an oligonucleotide probe used according to this invention can vary considerably in length. The preferred length will depend on considerations such as the target nucleic acid length, length of the nucleotide sequence of interest, target nucleic acid type (i.e., DNA or RNA), target nucleic acid G-C content, and the spacing of fluorochromes on the probe. Preferably the length of the probe used in practicing this invention is from 20 to 200 nucleotides. More preferably, the length is from 40 to 100 nucleotides.

Regardless of probe length, the probe can vary in nucleotide sequence. The nucleotide sequence of a probe used in this invention will depend on the sequence of the target nucleic acid. The probe's nucleotide sequence must have sufficient complementarity to the target nucleic acid to allow hybridization with the target nucleic acid under the chosen in situ hybridization conditions. Preferably, base pair matching between the probe and target nucleic acid is at least 80%. More preferably, the base pair matching is approximately 100%.

Methods of synthesizing DNA generally, including oligonucleotide probes useful in practicing this invention, are well known. For a general discussion of oligonucleotide synthesis, see Caruthers, "Synthesis of Oligonucleotides and Oligonucleotide Analogs," in *Topics in Molecular and Structural Biology, Vol.* 12: *Oligodeoxynucleotides* (Cohen, ed.), MacMillan Press, London, pp. 9–24. Apparatuses for automated DNA synthesis are commercially available. Preferably automated DNA synthesis is employed in obtaining probes used in the practice of this invention.

Typically, an oligonucleotide probe for use in practicing this invention is obtained in a two step process. The first step is the synthesis of an oligonucleotide comprising a modified base at each position in the nucleotide sequence where a fluorochrome label is desired. The second step is the covalent attachment of a fluorochrome label to each modified base.

The purpose of the modified base used in the first step is to provide a functional group through which the fluorochrome label is covalently attached to the oligonucleotide in the second step. Preferably, the functional group on the modified base is a primary amino group. Preferably, the functional group is at the end of a spacer arm.

During synthesis of an oligonucleotide, the functional group on the modified base (for attachment of the protection moiety) typically bears a protecting (blocking) group, e.g., a trifluoroacetamide group. One of skill in the art will recognize that the protecting group must be removed by a suitable chemical reaction before the functional group can be used for attachment of the fluorochrome label.

Figure 3A:
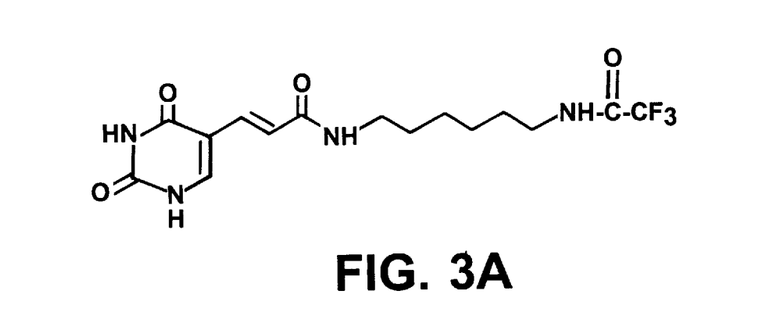
FIG. 3A is the chemical formula of a preferred modified base.
Figure 3B:
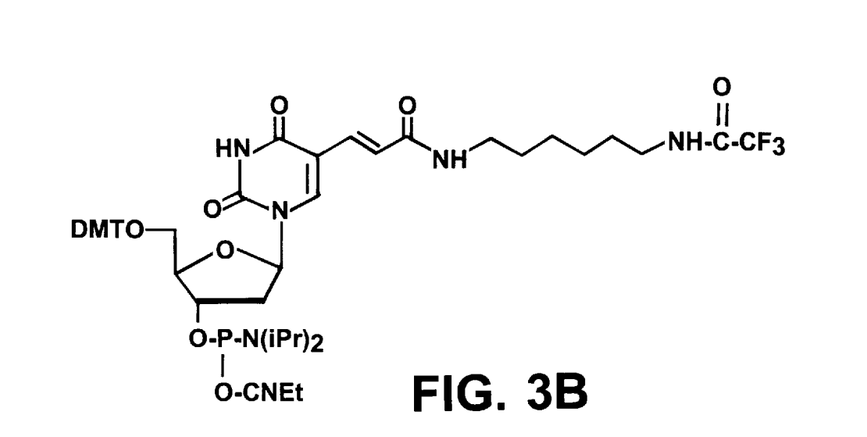
FIG. 3B is the chemical formula of a preferred deoxynucleotide analog comprising the modified base of FIG. 3A.

For preparation of amino modified bases, see, e.g., Jablonski et al. *Nucleic Acids Res.* 14: 6115–6128 (1986) and Ruth, *DNA* 3: 123 (1984). A particularly preferred modified base is a thymine analog with the chemical structure shown in FIG. 3A. The thymine analog depicted in FIG. 3A can be conveniently incorporated into an oligonucleotide by means of a dT analog whose structure is shown in FIG. 3B. The dT analog depicted in FIG. 3B is available commercially as "Amino-Modifier C6 dT" (Glen Research, Sterling, Va.), which is designed for use in conventional automated DNA synthesis. The trifluoroacetamide group on "Amino-Modifier C6 dT" is a protecting group. It is removed by hydrolysis during deprotection, to expose a primary amine group for use in attachment of a protection moiety.

The total number, and the spacing, of the modified bases (and covalently attached fluorochrome labels) in the oligonucleotide can vary. Preferably, a modified base is incorporated within five bases from the 3' end of the oligonucleotide.

It is preferable to incorporate a modified base at approximately every tenth base position in the nucleotide sequence of the oligonucleotide. Incorporation of modified bases, and thus fluorochrome labels, closer than every ten bases causes quenching of fluorescence and concomitant loss of visual signal strength.

Various fluorochromes are useful in practicing this invention. Preferably the fluorochrome is CY3 (Biological Detection Systems, Pittsburgh, Pa.), fluorescein (Molecular Probes, Inc., Eugene, Oreg.), or Texas red (Molecular Probes, Inc., Eugene, Oreg.). CY3 is particularly preferred. The advantages of CY3 include: (1) high molar extinction coefficient for absorption of light at excitation wavelength, (2) high quantum efficiency of emission, (3) pH insensitivity, and (4) good water solubility. Water solubility reduces nonspecific adsorption to membranes, which results in lower background.

For standard methods of attaching fluorochromes onto amino groups, see Agrawal et al. *Nucleic Acids Res.* 14: 6227–6245 (1986).

Target Nucleic Acids

The target nucleic acid can be DNA or RNA. The target nucleic acid can be located in the target cell's nucleus or cytoplasm. Examples of target nucleic acids include target cell mRNA, pre-mRNA, or chromosomal DNA, or viral RNA or DNA present in the target cell.

Typically, the target nucleic acid molecule is mRNA native to the target cell or single-stranded viral RNA present in the target cell, or a particular allele on a chromosome. Examples of other nucleic acid target molecules include chromosomes containing an expanded trinucleotide repeat.

Examples of target molecules other than nucleic acids include membrane receptor proteins and muscle filament proteins. When this invention is practiced with a target molecule other than a nucleic acid, the fluorochrome-labeled probe must be a ligand or specific binding partner of the target molecule. The selection of such ligands or specific binding partners is within ordinary skill in the art.

In Situ Hybridization

In situ hybridization methods are well known in the art. See, e.g., Singer et al., "optimization of in situ hybridization using isotopic and nonisotopic detection methods," *Biotechniques* 4: 230–250 (1986).

Experimental Information

In Situ Hybridization of Beta and Gamma-Actin mRNA

Immediately before hybridization, cells were permeabilized for 5 minutes in acetone (HPLC grade) at −20° C. and washed in PBS for 5 to 10 minutes. Beta- and gamma-actin mRNAs were detected by a single step in situ hybridization technique using synthetic 50–53 mer, approximately 50% GC rich, fluorochrome labeled synthetic DNA oligomer probes specific to sequences of the 3' and 5' untranslated regions (3' UTR and 5' UTR) of rat beta-actin mRNA and the 3' UTR of gamma-actin mRNA.

Five oligonucleotide probes of equal length, complementary to five non-overlapping regions of the 3' UTR of beta actin or gamma-actin, were synthesized.

Three oligonucleotide probes of equal length, complementary to the 5' UTR of the beta-actin gene was also synthesized. Various combinations of these probes were used to detect actin mRNAs.

Simultaneous hybridization to beta- and gamma-actin mRNAs is described here to illustrate the method. Twenty nanograms each of the beta- and gamma-actin 3'-UTR probes, labeled with fluorescein and CY3 respectively, and 20 micrograms each of sonicated salmon sperm and *E. coli* tRNA were combined in a 1.5 ml Eppendorf tube, dried down in a SPEEDVAC®, and subsequently taken up in 10 microliters of 100% formamide. This solution was heated at 72° C. for 2 minutes and then diluted with 10 microliters of hybridization buffer containing 1:2:2 of BSA (Boehringher Manneheim 20 mg/ml), 20× SSC and water. The resulting hybridization mixture of 50% formamide and 0.6M sodium was placed on parafilm, immediately covered with a coverslip and incubated at 37° C. in a humidified incubator in the dark for 3.5 to 4.0 hours.

Each coverslip was then washed in 3 ml of 50% formamide and 2× SSC (0.3M sodium) for 0.5 hour at 37° C., and 2 times in 3 ml of 1× SSC for 15 minutes, mounted on slides in a mounting medium which also contains dual labeled fluorescein and rhodamine 100 nm latex beads. The coverslip was sealed with clear nail polish and subsequently stored at −20° C.

Phenylenediamine was included in the mounting medium for its antioxidant properties, which properties advantageously prevent or retard photobleaching.

Detection of actin mRNA using Digital Imaging Fluorescence Microscopy

A digital imaging microscope system comprising a Nikon DIAPHOT™ inverted epifluorescence microscope modified to collect images under computer control was used to collect digitized optical sections, which were used to generate 3D images of fluorescent probes in cells. The samples were illuminated with a mercury lamp, using dichroic filters for excitation, and emission wavelengths of 535 nm and 590 nm, respectively, for rhodamine and 485 nm and 530 nm, respectively, for fluorescein. Light was collected with a Nikon 60× planapochromat objective with a numerical aperture of 1.4 combined with a 2.5× or 5.0× photo eyepiece. Collected light was detected with a cooled CCD camera (Photometrics Inc., Tucson, Ariz.). Pixel diameter was 20 micrometers. Dynamic range was 1:16383 (14 bit).

A series of 20–30 optical sections were acquired at 0.25 or 0.10 micrometer intervals using a 2000 millisec exposure time for CY3, and a 3000 to 4000 millisec exposure time for fluorescein, per interval. Fluorescent (rhodamine or fluorescein) beads with a diameter of 200 nm were mounted on separate slides, but in an aliquot of the same mounting media used for the cells, and were optically sectioned, (50 or 60 optical sections) at 0.25 or 0.10 micrometer intervals. The resulting bead images were used to determine the rhodamine and fluorescein point spread functions of the optical system. The number of optical sections used for the point spread function was at least 2-fold greater than the number of optical sections used for imaging. The resulting point spread function was used in the subsequent EPR 3D image restoration process.

A Silicon Graphics Indigo 2 Graphics Extreme workstation was used for image processing and analysis. Images were restored at 200 to 400 iterations and at alpha values of 0.00001 and 0.000005, respectively. Other commercially available workstations can also be used.

Determination of Total Fluorescence Intensity (TFI) of a Single Fluorochrome in Cell Imaging Environment To determine whether small punctate signals observed in nuclei represent clusters of mature mRNAs or individual beta-actin mRNA molecules, a method for measuring the emission intensity of a single fluorochrome was developed. From the TFI value for a single fluorochrome, the intensities associated with a specific number of oligonucleotide probes hybridized to a single mRNA could be calculated and compared to observed fluorescence signal intensities.

Five oligonucleotide probes, each being 50–52 nucleotides in length and complementary to non-overlapping regions of rat beta-actin 3'-UTR MRNA, were synthesized. Each probe was labeled with five fluorochromes, each at a predetermined base position. Fluorochromes used were either CY3 or fluorescein. The fluorochromes were covalently attached to modified thymine residues separated by 7 to 13 nonlabeled nucleotides. Such spacing of fluorochromes minimizes quenching.

The five probes were labeled either in separate labeling reactions or in a common labeling reaction containing an equimolar mixture of all five probes. The labeled probes (individually or in a mixture of all five) were purified by conventional gel electrophoresis and stored as an aqueous stock solution. The aqueous stock solutions had probe concentrations of 0.1–1.0 micrograms per microliter (determined by 260 nm UV absorption).

To determine the TFI of a single fluorochrome in an environment closely approximating the fluorescence in situ hybridization imaging environment, it was necessary to prepare solutions of labeled probes in mounting media. Two successive dilutions were prepared. The first dilution was prepared using 100% glycerol. The second dilution was prepared using an aliquot of mounting medium (90 ml glycerol, 10 ml PBS, and 100 mg phenylenediamine, pH 8.5).

Stock solutions of 10 nanograms per microliter in glycerol were prepared for each labeled probe by diluting 10 microliters of each probe stock solution with an appropriate amount of glycerol and mixing well. All vials were tared and all pipetted solutions were weighed. Carefully pipetted volumes were used to prepare dilutions in the desired ranges. To maximize accuracy, however, probe concentrations were calculated using values obtained by weighing solutions and converting solution weights to volumes. All manipulations involving fluorochromes were carried out as quickly as possible, under reduced illumination.

Final working dilutions containing between 1 and 15 nanograms per microliter were prepared by diluting aliquots of the 10 nanograms per microliter glycerol stock solution with mounting media containing either a dilute suspension of red or green fluorescent latex beads.

Green fluorescent latex beads were used with CY3 labeled oligomers. Red fluorescent latex beads were used with fluorescein labeled oligomers.

It was assumed that the specific gravity of a solution of glycerol and 10% water will be close to that of 100% glycerol, i.e., 1.25 grams per milliliter. It was further assumed that using this value once would not contribute a significant error to the final calculation.

The following exemplifies the preparation of a final working dilution of a probe solution. Ten microliters (i.e., 0.01162 grams) of glycerol stock containing 92.5 nanograms of oligomer was diluted to 50 microliters with mounting media. The mass of the final solution in mounting media was 0.06103 grams. The final volume was calculated to be 48.8 microliters. The final oligomer concentration was 1.89 ng/$\mu$l.

Five $\mu$l of a probe solution (final working dilution) was placed on a glass slide, covered with a 22 mm×0.1 mm glass coverslip (pretreated with Salmon Sperm DNA to retard adsorption of the DNA to the coverslip), and sealed with nail polish. The beads were allowed to settle on the glass surfaces before measurements were taken.

The TFI contributed by a single fluorochrome was measured under conditions essentially identical to the conditions used in imaging cells subjected to in situ hybridization. Therefore, it was necessary to acquire an image of the fluorochrome labeled oligonucleotide solution between a 0.1 mm coverslip and microscope slide. To calculate the number of fluorochromes imaged, an accurate measurement of the imaged volume of solution was necessary. Knowing the imaged volume, probe concentration and number of fluorochromes per probe allowed calculation of the number of fluorochromes in the imaged volume.

For a 60× objective and 2.5× photo eyepiece, a pixel represents a 187×187 nm$^2$ area at the sample site. For a 60× objective and 5.0× photo eyepiece, a pixel represents a 93×93 nm$^2$ area at the sample site.

A single optical section of the fluorochrome labeled oligomer solution was imaged at ½ the distance between coverslip and slide in the appropriate filter set with the same exposure times used for imaging hybridized cells. A single optical plane contains the total fluorescence intensity of the imaged rectangular volume. For z axis distances less than 100 micrometers, there is negligible light lost through self absorption. The measured z axis distances for different slides ranged from 2.5 to 14 microns.

A control containing mounting media only was also imaged. The TFI per unit volume determined for this control was used to correct for background contributions to the TFI of probe solutions. This background contribution was about 1–2%, which is almost negligible at the concentrations used in this study.

Using the measured TFI of the imaged volume, the TFI per fluorochrome was calculated. The calculated molecular weights for the respective probes were based on unmodified deoxynucleotide molecular weights, since the original oligomer concentration determination at 260 nm absorption was also based on the absorption maxima of deoxyribonucleotides. The assumption is that the five fluorochrome residues of each probe have a minimum contribution to the absorbance at 260 nm.

The single imaged optical plane contains the total light emitted by all fluorochromes above and below the imaged plane. Therefore the TFI of the single imaged plane divided by the total number of fluorochromes present in the imaged volume determines the TFI of a single fluorochrome.

Fluorescence emission intensities depend on excitation intensities, which vary due to lamp intensity, aperture, alignment, etc. Therefore, the TFI per fluorochrome was determined during each imaging session.

Quantitative Analysis of Actin mRNA Using Digital Imaging Fluorescence Microscopy The samples of cells subjected to in situ hybridization were imaged by collection of 20 to 30 optical sections per image. Exposure times were 2000 msec for the CY3, and 3000 or 4000 msec per optical section for fluorescein images. Solutions of a known concentration of the fluorochrome labeled oligomer probes were imaged during the same session to allow quantitation of the hybridized probes.

The images were prepared for restoration using standard algorithms that subtract dark current and background and normalize the image intensities in each optical section to the total intensity of the first optical section. Normalization to the first optical section corrects photobleaching effects in the subsequent sections. The prepared images were processed using EPR, a known restoration algorithm which reassigns the collected light from each optical section to its original point source. The restoration is carried out using 200 to 400 iterations and an alpha value of 0.00001 or 0.000005, respectively. That accomplished 0.003 convergence to discrete point sources.

To ensure maximal sensitivity for low intensity signals, the restorations were run with a scaling factor of 1.0. In this mode, however, pixel intensity values generated during the restoration process which exceed 32,767 grey levels are truncated to 32,767. Therefore, to guard against the possible saturation of the restored signal at the very intense transcription sites, the autoscale mode was used to do an alternative restoration of the nuclei. In this mode, the most intense pixel of the restored image is assigned a value of 32,767 and all other pixel values are scaled linearly relative to this brightest pixel on a scale of 0 to 32,767.

Upon completion of a restoration using the autoscaling mode, a scaling correction was applied to normalize the pixel intensity values from the autoscaled image to those from an image with a 1.0 scaling. This allowed comparison of the absolute TFI values at the transcription sites with the absolute TFI values of the low level signal intensities after restoration.

A threshold was established and applied to restored images. All pixels with values less than a minimum TFI were set to zero. The threshold level was determined by analyzing the TFI distribution histogram of non-zero pixels in a cell subjected to a mock hybridization and restored with a scaling of 1.0. A value 3 standard deviations above the mean TFI per pixel in these background images was chosen as the threshold level. That eliminates greater than 95% of the low level background pixel without approaching the intensity value of a bona fide signal. The threshold value was adjusted by the appropriate scaling factor for images restored with the autoscaling option.

The restored images were imported into the Data Analysis and Visualization Environment ("DAVE"), using threshold values appropriate to the respective fluorescein and CY3 images. Bona fide signal was then detected and mapped by comparing the TFI of a discrete object in the image with the expected TFI for a bona fide signal which has been predetermined from the TFI per fluorochrome, e.g., with a standard algorithm.

Figure 2A:
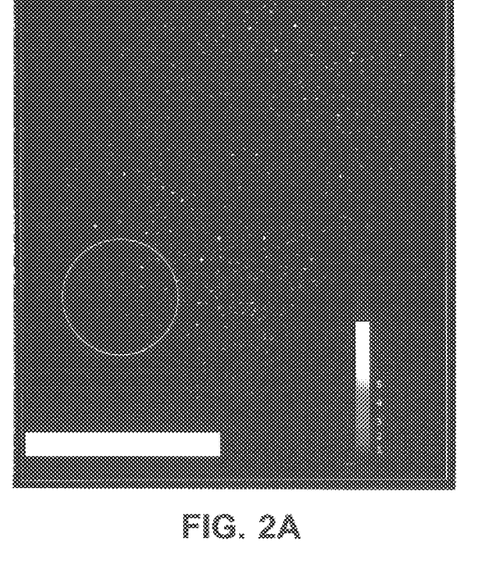
FIG. 2A is a restored image of a cell subjected to in situ hybridization using five 50-nucleotide probes directed to non-overlapping sequences in the 3'UTR of beta-actin mRNA. The restored image is presented as a heat map. Objects are color coded according to the number of hybridized probes present: green, one; blue, two; pink, three; red, four; and yellow, five.
Figure 2B:
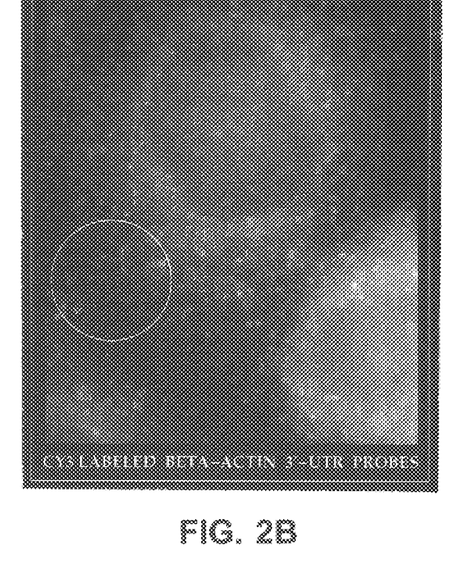
FIG. 2B is a representative non-processed optical section used in producing the heat map shown in FIG. 2A.

The analysis of the point sources was used to generate a heat map. In the heat map, signals representing one probe were of the coolest hue (green) and signals representing five probes hybridized were of the hottest hue (yellow). The heat map suggested that most signals represented individual mRNA molecules with fewer than the maximum number of probes hybridized. An example of this heat map is shown in FIG. 2A.

The five probes hybridizing to the 3'-UTR of either beta- or gamma-actin mRNA represented a total length less than 461 nucleotides and 448 nucleotides for beta- and gamma-actin respectively. For a fully extended 3'-UTR region of mRNA, this number of nucleotides would translate to a length of 138 and 134 nm respectively for beta- and gamma-actin mRNA using 3 angstroms as the average length per nucleotide. A pixel represented 187×187 $nm^2$ of a cell when the 60× objective and 2.5× camera eyepiece were used. Therefore, the signal from five 3'-UTR probes hybridized to a single actin mRNA theoretically could be encompassed by a single pixel.

A restored image of a 100 nm rhodamine or fluorescein-labeled bead was generated using the same number of iterations as used for cell imaging. The restored 100 nm bead was used as a model for the size and shape of signal expected for an object emitting light from an area encompassing one pixel, i.e., 187 $nm^2$. At 400 iterations and an alpha value of 0.000005, a 100 nm bead typically did not exceed 12 voxels, with the greatest dimension occurring in the z-axis.

Signal from the in situ hybridization of beta- and gamma-actin mRNA was analyzed in 3D. Contiguous voxels containing signal in the restored images after thresholding were treated as single objects. The object was then defined by the total TFI of the contiguous voxels, by the number of contiguous voxels and by the co-ordinate of the voxel of maximum intensity.

Detection of a Single Copy Gene

In situ hybridization of 10 unique CY3-labeled oligonucleotide probes directed to the template strand of the beta-actin gene was used as an alternative method to measure the TFI associated with a single fluorochrome on a hybridized DNA oligomer probe. This provided a more nearly identical environment to that of the probes hybridized to mRNA in situ, because the probe was hybridized to an immobilized DNA strand rather than being in solution.

The beta-actin gene locus was used as a single copy hybridization site. Each of the 10 probes specific to the actin gene was conjugated to 6 fluorochromes. Therefore, no more than 60 fluorochromes could contribute to the TFI at the gene locus. The TFI measured at the gene locus in a restored image was compared to the theoretical value expected for the maximum number of hybridized probes, i.e., 10. The images with the most intense signal at the actin gene loci show the predicted TFI for 10 probes, confirming the TFI per fluorochrome measurements. In an additional confirmation experiment, a probe containing a known number of fluorochromes was affixed to glass and imaged under conditions identical to sample imaging conditions.

Detection of Nuclear and Cytoplasmic Beta-Actin mRNA Using Digital Imaging Microscopy Digitally imaged cells subjected to in situ hybridization with CY3 labeled beta-actin 3'-UTR probes showed discrete punctate signals dispersed throughout the cytoplasm. The small punctate signals were most easily discernible in the thinner peripheral cytoplasmic regions of the cell, but were clouded in out of focus light in the thicker perinuclear regions. Similar small punctate signals were also detected in the nucleus of serum induced cells between 5 and 15 minutes after serum induction. The greatest concentration occurred proximal to the intense signal of the actin transcript sites. Cells subjected to in situ hybridization with fluorescein-labeled beta-actin 3' UTR probes showed a faint punctate texture in the cytoplasm. That was distinguishable from the appearance of control a cell subjected to mock hybridizations with no probe.

The fluorescein signal was less intense than the CY3 signal from otherwise identical probes, but the fluorescein signal was bright at the transcription sites. With the fluorescein-labeled probes, there were notably fewer punctate signals emanating from, or in close proximity to, the nuclear transcription sites, as compared to results observed when using CY3-labeled probes.

Single mRNA Detection

The TFI values predicted for a single fluorescein fluorochrome and a single CY3 fluorochrome were converted to TFI values expected for 1–5 oligomer probes hybridized to the 3'-UTR of a single beta- or gamma-actin MRNA for a given imaging session.

Cells subjected to in situ hybridization with beta- or gamma-actin CY3 labeled probes were subjected to digital imaging fluorescence microscopy. The resulting optical sections were used to generate restored images. The restored images were subjected to threshold application and analyzed using DAVE, as described above. All nuclear and cytoplasmic signals were analyzed as 3D objects. The objects were located, sized, counted and sorted according to total intensity.

All objects in the nucleus (except the transcription sites), and most objects in the cytoplasm, displayed intensities in the range predicted for hybridization of 1–5 probes to a single mRNA. This result was obtained when CY3-labeled 3' UTR probes for beta- or gamma-actin mRNA were used.

All objects with a TFI falling into the range expected for a single mRNA also have a size which falls into a range expected for an object theoretically occupying a single pixel. A fully extended 3'UTR spanning the hybridization sites would not exceed a length represented by a single pixel. Some objects in the cytoplasm appeared to exceed this size, even though the TFI fell into the range for a single mRNA. Such objects appeared to comprise two distinct entities, often connected by a pixel near the threshold value. The low level intensity pixel contiguous to both objects caused them to be counted as a single object by the DAVE counting algorithm.

This category of objects may represent two distinct objects approaching the 200 nm limit of resolution at the light microscope level. The individual TFIs of such connected objects corresponded to 1, 2 or 3 hybridized probes, i.e., the most prevalent extent of hybridization detected in the nucleus and cytoplasm for distinctly individual objects.

The TFI of the fluorescein probes was about 6–7 fold weaker than that of the CY3-labeled probes. Therefore, hybridization targets with fewer than four or five fluorescein labeled 3'-UTR probes were indistinguishable from background. This would account for the small number of punctate signals observed in cells hybridized with fluorescein labeled 3'UTR probes. This is because data obtained using CY3-labeled probes showed that most actin mRNA molecules detected carried one, two or three hybridized 3'UTR probes.

Co-Localization of Fluorescein-labeled Probes and CY3-labeled Probes Hybridized to Beta-actin mRNA Three fluorescein-labeled probes complementary to the 5'UTR, and five probes complementary to the beta-actin coding region were mixed with the five CY3-labeled probes complementary to the 3'-UTR of beta-actin mRNA. The mixture was hybridized to quiescent and serum-stimulated NRK cells. The hybridization resulted in a co-localization of both fluorescein and CY3 signals on the same beta-actin mRNA molecule in situ.

Other embodiments of the invention are within the following claims.

We claim:

1. A method for digital imaging fluorescence microscopy detection of an individual nucleic acid probe bound to a nucleic acid target molecule in a sample, said method comprising the steps of:
   (a) obtaining a fluorochrome-labeled nucleic acid probe wherein the number of fluorochromes per probe is predetermined;
   (b) contacting said labeled probe with a nucleic acid target molecule under conditions allowing said labeled probe to bind to said target molecule;
   (c) removing unbound labeled probes from labeled probes bound to target molecules;
   (d) detecting, by digital imaging fluorescence microscopy, said labeled probe bound to said target molecule, wherein said digital imaging fluorescence microscopy includes digitally recording a series of optical sections;
   (e) determining the total fluorescence intensity per fluorochrome under imaging conditions;
   (f) determining the total fluorescence intensity per probe from said total fluorescence intensity per fluorochrome;
   (g) normalizing said total fluorescence intensity per fluorochrome under imaging conditions to a value for a single conjugated fluorochrome whose image is acquired through a series of optical sections and restored, thereby producing a normalized total fluorescence intensity;
   (h) producing a prepared image from said series of optical sections by subjecting said series of optical sections, sequentially, to dark current subtraction, background subtraction, and normalization to the first optical section;
   (i) producing a restored image;
   (j) identifying discrete objects in said restored image, said objects corresponding to target molecules;
   (k) comparing said normalized total fluorescence intensity to values of objects in said restored image;
   (l) determining the presence of one or more probes in one of said objects, thereby detecting an individual nucleic acid probe bound to a nucleic acid target molecule in a sample.

2. The method of claim 1, wherein said restored image is produced by subjecting a prepared image to exhaustive photon reassignment.

3. The method of claim 2, wherein a threshold is applied to pixels in said restored image by preparing a restored image of a negative control cell subjected to a mock in situ hybridization protocol wherein no probe is present, and selecting a total fluorescence intensity threshold value based on one or more measurements relating to said negative control cell.

4. The method of claim 1, wherein said probe is an oligonucleotide linked to a fluorochrome label, said target molecule is a nucleic acid, and said binding is in situ nucleic acid hybridization.

5. The method of claim 4, wherein the length of said oligonucleotide is from 20 to 200 nucleotides.

6. The method of claim 5, wherein the length of said oligonucleotide is from 40 to 100 nucleotides.

7. The method of claim 4, wherein said fluorochrome label is covalently attached to a functional group on a modified base incorporated into said oligonucleotide.

8. The method of claim 7, wherein said functional group is a primary amino group.

9. The method of claim 7, wherein said functional group is at the end of a spacer arm.

10. The method of claim 4, wherein said oligonucleotide comprises a multiplicity of modified bases with attached fluorochromes.

11. The method of claim 10, wherein said modified bases are incorporated at intervals of seven to thirteen base positions in the nucleotide sequence of said oligonucleotide.

12. The method of claim 1, wherein the fluorochrome is selected from the group consisting of CY3 and fluorescein.

13. The method of claim 4, wherein said nucleic acid is a DNA molecule.

14. The method of claim 4, wherein said nucleic acid is an RNA molecule.

15. The method of claim 1, wherein said total fluorescence intensity per fluorochrome under imaging conditions is determined by a method comprising the steps of:
(a) providing a microscope slide and coverslip;
(b) providing on the surface of said microscope slide a first fluorescence point source;
(c) providing on the surface of said coverslip a second fluorescence point source;
(d) preparing a standard solution containing a known concentration of fluorochrome-labeled probes;
(e) placing a suitable volume of said standard solution between and in contact with said microscope slide and said coverslip, said first fluorescence point source and said second fluorescence point source being within the field of view of said digital imaging microscopy system;
(f) determining a distance between said first and second fluorescence point sources, thereby obtaining a z axis distance between said microscope slide and said coverslip;
(g) determining an imaged volume by determining the product of an x axis distance, a y axis distance, and said z axis distance;
(h) determining the total amount of probe fluorescence from the imaged volume;
(i) calculating the total number of probes in the imaged volume using (1) said known concentration of probes in said standard solution, and (2) said imaged volume; and
(j) dividing the total amount of probe fluorescence from said imaged volume by the number of fluorochromes in the imaged volume to determine the total fluorescence intensity of a single fluorochrome under imaging conditions.

16. The method of claim 3, wherein said threshold is determined and applied to a sample by:
(a) preparing a restored image of a negative control cell subjected to a mock in situ hybridization protocol wherein no probe is present;
(b) obtaining a frequency distribution of light in said negative control cell and calculating the mean and standard deviation of said frequency distribution;
(c) selecting a total fluorescence intensity threshold value based on said mean and standard deviation;
(d) excluding all optical data other than that originating from within the sample, thereby producing a masked image; and
(e) setting to a value of zero all pixels whose total fluorescence intensity value is below said total fluorescence intensity threshold value in said masked image.

17. The method of claim 2, wherein said nucleic acid is a viral nucleic acid, and said method is used to diagnose a viral infection.

18. The method of claim 17, wherein said viral infection is HIV infection.

19. The method of claim 4, wherein said nucleic acid is a chromosome, and said method is used to diagnose a genetic defect.

20. The method of claim 19, wherein said genetic defect is a trinucleotide repeat expansion.

21. The method of claim 1, wherein the presence of one or more probes in an object is determined based on the total fluorescence intensity of said object and the total fluorescence intensity per probe.

22. A method for determining the total fluorescence intensity of a single fluorochrome in a digital imaging microscopy system, under imaging conditions, said method comprising the steps of:
(a) providing a microscope slide and coverslip;
(b) providing on the surface of said microscope slide a first fluorescence point source;
(c) providing on the surface of said coverslip a second fluorescence point source;
(d) preparing a standard solution containing a known concentration of fluorochrome-labeled probes;
(e) placing a suitable volume of said standard solution between and in contact with said microscope slide and said coverslip, said first fluorescence point source and said second fluorescence point source being within the field of view of said digital imaging microscopy system;
(f) determining a distance between said first and second fluorescence point sources, thereby obtaining a z axis distance between said microscope slide and said coverslip;
(g) determining an imaged volume by determining the product of an x axis distance, a y axis distance, and said z axis distance;
(h) determining the total amount of probe fluorescence from the imaged volume;
(i) calculating the total number of probes in the imaged volume using (1) said known concentration of probes in said standard solution, and (2) said imaged volume; and
(j) dividing the total amount of probe fluorescence from said imaged volume by the number of fluorochromes in the imaged volume to determine the total fluorescence intensity of a single fluorochrome under imaging conditions.

23. The method of claim 22, wherein said first fluorescence point source and said second fluorescence point source are beads bearing a fluorochrome label.

24. The method of claim 23, wherein said beads have a diameter between 50 and 800 nanometers.

25. The method of claim 23, wherein said beads have a diameter between 100 and 400 nanometers.

26. The method of claim 23, wherein said beads have a diameter of approximately 200 nanometers.

27. A kit for use in determining the total fluorescence intensity of a single fluorochrome in a digital imaging microscopy system under imaging conditions, said kit comprising:
(a) a spotted microscope slide comprising fluorescent material on at least one surface, said material being deposited on said surface as a discrete slide spot, thereby forming a spotted microscope slide surface, said slide spot having a diameter and a thickness between 1 and 400 nanometers; and
(b) a spotted coverslip comprising fluorescent material on at least one surface, said material being deposited on said surface as a discrete coverslip spot, thereby forming a spotted coverslip surface, said coverslip spot having a diameter and a thickness between 1 and 400 nanometers;
wherein said spotted microscope slide and said spotted coverslip can be used in combination, with said spotted microscope slide surface and said spotted coverslip surface opposing each other, so that said microscope slide spot and said coverslip spot are simultaneously visible within the field of view of a microscope.

* * * * *